(12) United States Patent
Kim et al.

(10) Patent No.: US 9,839,369 B2
(45) Date of Patent: Dec. 12, 2017

(54) METHOD AND USER INTERFACE DEVICE FOR DISPLAYING ELECTROCARDIOGRAMS

(75) Inventors: Ye-Hoon Kim, Seoul (KR); Keun-Joo Kwon, Seoul (KR); Seok-Jin Hong, Hwaseong-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 1200 days.

(21) Appl. No.: 13/454,634

(22) Filed: Apr. 24, 2012

(65) Prior Publication Data

US 2013/0109988 A1    May 2, 2013

(30) Foreign Application Priority Data

Nov. 2, 2011    (KR) .................. 10-2011-0113531

(51) Int. Cl.
*A61B 5/044*    (2006.01)
*A61B 5/0452*    (2006.01)
*A61B 5/00*    (2006.01)

(52) U.S. Cl.
CPC ............ *A61B 5/044* (2013.01); *A61B 5/0452* (2013.01); *A61B 5/742* (2013.01)

(58) Field of Classification Search
CPC .............................. A61B 5/044; A61B 5/0452
USPC ......................................... 600/509, 515, 523
See application file for complete search history.

(56) References Cited

U.S. PATENT DOCUMENTS

2009/0156908 A1* 6/2009 Belalcazar ........... A61B 5/0031
    600/301
2010/0049067 A1* 2/2010 Paine ................... A61B 5/0452
    600/509

* cited by examiner

*Primary Examiner* — Christopher D Koharski
*Assistant Examiner* — Roland Dinga
(74) *Attorney, Agent, or Firm* — NSIP Law

(57) ABSTRACT

A method of displaying electrocardiograms comprises displaying a reference electrocardiogram; and displaying a measured electrocardiogram so that the reference electrocardiogram and the measured electrocardiogram are displayed in an overlapping state.

27 Claims, 11 Drawing Sheets

METHOD AND USER INTERFACE DEVICE FOR DISPLAYING ELECTROCARDIOGRAMS

CROSS-REFERENCE TO RELATED APPLICATIONS

This application claims the benefit under 35 USC 119(a) of Korean Patent Application No. 10-2011-0113531 filed on Nov. 2, 2011, in the Korean Intellectual Property Office, the entire disclosure of which is incorporated herein by reference for all purposes.

BACKGROUND

1. Field

The following description relates to a medical instrument for diagnosis, and more particularly, to a method of displaying electrocardiograms and a user interface device capable of more easily analyzing the electrocardiograms.

2. Description of Related Art

An electrocardiogram is an important means for diagnosing heart-related diseases. After the electrocardiogram of a patient is measured for a predetermined time, the results must be read. Since very similar waveforms are continuously produced, it is very difficult to observe only the waveforms to identify an abnormal state and a degree of abnormality.

A variety of methods of displaying the electrocardiogram are known. For example, the methods include a method of displaying the electrocardiogram divided according to a beat, a method of displaying only abnormal portions of the electrocardiogram, a method of displaying a plurality of beats accumulated on one screen, and so on. However, although these methods provide some pieces of information that a medical doctor requires to read the electrocardiogram, they are still insufficient to show intuitive information. Moreover, a user interface used for these methods is complicated.

SUMMARY

According to an aspect, method of displaying electrocardiograms includes displaying a reference electrocardiogram; and displaying a measured electrocardiogram so that the reference electrocardiogram and the measured electrocardiogram are displayed in an overlapping state.

The reference electrocardiogram and the measured electrocardiogram each may include at least one beat; each beat of the reference electrocardiogram and the measured electrocardiogram may include a plurality of waves; and the displaying of the measured electrocardiogram may include aligning the reference electrocardiogram and the measured electrocardiogram with each other based on at least one of the plurality of waves so that the reference electrocardiogram and the measured electrocardiogram are displayed as being aligned with each in the overlapping state.

The plurality of waves may include P, Q, R, S, and T waves; and the aligning of the reference electrocardiogram and the measured electrocardiogram with each other may include aligning the reference electrocardiogram and the measured electrocardiogram with each other based on a peak of at least one of the P, Q, R, S, and T waves.

The aligning of the reference electrocardiogram and the measured electrocardiogram with each other may further include expanding or compressing the reference electrocardiogram or the measured electrocardiogram on a time axis based on an alignment reference point in each beat so that the reference electrocardiogram and the measured electrocardiogram are displayed as being aligned with each other at a same alignment reference point in each beat in the overlapping state.

The aligning of the reference electrocardiogram and the measured electrocardiogram with each other may further include expanding or compressing the reference electrocardiogram or the measured electrocardiogram on a time axis based on an alignment reference point in a plurality of beats so that the reference electrocardiogram and the measured electrocardiogram are displayed as being aligned with each other at a same alignment reference point in the plurality of beats in the overlapping state.

The reference electrocardiogram may be extracted from a plurality of measured electrocardiograms by a statistical method, or is obtained from a predetermined standard model.

The method may further include generating a visualization of a deviation between the reference electrocardiogram and the measured electrocardiogram displayed in the overlapping state; and displaying the visualization of the deviation overlapping the display of the reference electrocardiogram and the measured electrocardiogram in the overlapping state.

The method may further include generating a visualization of a deviation between the reference electrocardiogram and the measured electrocardiogram displayed in the overlapping state for a basic unit including at least one beat; and displaying the visualization of the deviation separately from the display of the reference electrocardiogram and the measured electrocardiogram in the overlapping state.

The basic unit may include a plurality of beats.

The method may further include ranking the deviation within a reference range; and displaying the ranking of the deviation.

According to an aspect, a method of displaying electrocardiograms includes receiving a reference electrocardiogram and a measured electrocardiogram each including at least one beat; aligning the reference electrocardiogram and the measured electrocardiogram with each other; and displaying a deviation between the reference electrocardiogram and measured electrocardiogram aligned with each other for a basic unit including at least one beat.

Each beat of the reference electrocardiogram and the measured electrocardiogram may include a plurality of waves; and the aligning of the reference electrocardiogram and the measured electrocardiogram with each other may include aligning the reference electrocardiogram and the measured electrocardiogram based on at least one of the plurality of waves.

The basic unit may include a plurality of beats.

The method may further include ranking the deviation within a reference range; and displaying the ranking of the deviation.

According to an aspect, a user interface device for displaying electrocardiograms includes a first display window configured to display a reference electrocardiogram and a measured electrocardiogram each including at least one beat and aligned with each other in an overlapping state; and a second display window configured to display a deviation between the reference electrocardiogram and the measured electrocardiogram aligned with each other aligned with each other for a basic unit including at least one beat.

The reference electrocardiogram and the measured electrocardiogram each may include a plurality of waves constituting one beat; and the reference electrocardiogram and the measured electrocardiogram may be aligned with each other based on at least one of the plurality of waves.

The basic unit may include a plurality of beats.

The user interface device may further include a setting window that configured to receive a setting of an alignment criterion and/or a deviation display from a user.

According to an aspect, a method of displaying electrocardiograms includes obtaining a reference electrocardiogram; obtaining a measured electrocardiogram; aligning the reference electrocardiogram and the measured electrocardiogram with each other at at least one alignment reference point; and displaying the reference electrocardiogram and the measured electrocardiogram aligned with each other at the at least one alignment reference point in an overlapping state.

The reference electrocardiogram and the measured electrocardiogram each may include at least one beat; and the aligning may include aligning the reference electrocardiogram and the measured electrocardiogram with each other at at least one alignment reference point within each beat.

The reference electrocardiogram and the measured electrocardiogram each may include a plurality of beats; the aligning may include aligning the reference electrocardiogram and the measured electrocardiogram with each other at at least one alignment reference point within a set of a plurality of beats; and the displaying may include displaying the reference electrocardiogram and the measured electrocardiogram aligned with each other at the at least one alignment reference point in an overlapping state for the set of a plurality of beats.

The reference electrocardiogram and the measured electrocardiogram each may include at least one beat; and the method may further include expanding and/or compressing the reference electrocardiogram and/or the measured electrocardiogram on a time axis so that a length of each beat of the reference electrocardiogram is equal to a length of each beat of the measured electrocardiogram when the reference electrocardiogram and the measured electrocardiogram aligned with each other at the at least one alignment reference point are displayed in the overlapping state.

The reference electrocardiogram and the measured electrocardiogram each may include a plurality of beats; and the method may further include expanding and/or compressing the reference electrocardiogram and/or the measured electrocardiogram on a time axis so that a length of a set of a plurality of beats of the reference electrocardiogram is equal to a length of a set of a plurality of beats of the measured electrocardiogram when the reference electrocardiogram and the measured electrocardiogram aligned with each other at the at least one alignment reference point are displayed in the overlapping state.

The reference electrocardiogram and the measured electrocardiogram each may include at least one beat; each beat of the reference electrocardiogram and the measured electrocardiogram may include a plurality of waves; and the at least one alignment reference point may include any one or any combination of the following: a start point of a beat; an end point of a beat; and a peak of at least one of the plurality of waves.

The reference electrocardiogram and the measured electrocardiogram each may include a plurality of beats; each beat of the reference electrocardiogram and the measured electrocardiogram may include a plurality of waves; and the at least one alignment reference point may include any one or any combination of the following: a start point of a set of a plurality of beats; an end point of a set of a plurality of beats; and a peak of at least one of the plurality of waves.

The method may further include generating a visualization of a deviation between the reference electrocardiogram and the measured electrocardiogram aligned with each other at the at least one alignment reference point; and displaying the visualization of the deviation overlapping with the display of the reference electrocardiogram and the measured electrocardiogram aligned with each other at the at least one alignment reference point in the overlapping state.

The method may further include calculating a deviation between the reference electrocardiogram and the measured electrocardiogram aligned with each other; generating a visualization of the deviation; and displaying the visualization of the deviation.

The reference electrocardiogram and the measured electrocardiogram each may include at least one beat; and the calculating may include calculating the deviation for one beat of each of the reference electrocardiogram and the measured electrocardiogram.

The reference electrocardiogram and the measured electrocardiogram each may include a plurality of beats; and the calculating may include calculating the deviation for a set of a plurality of beats of each of the reference electrocardiogram and the measured electrocardiogram.

The method may further include ranking the deviation within a reference range; and displaying the ranking of the deviation.

Other features and aspects will be apparent from the following detailed description, the drawings, and the claims.

DETAILED DESCRIPTION

Figure 1:
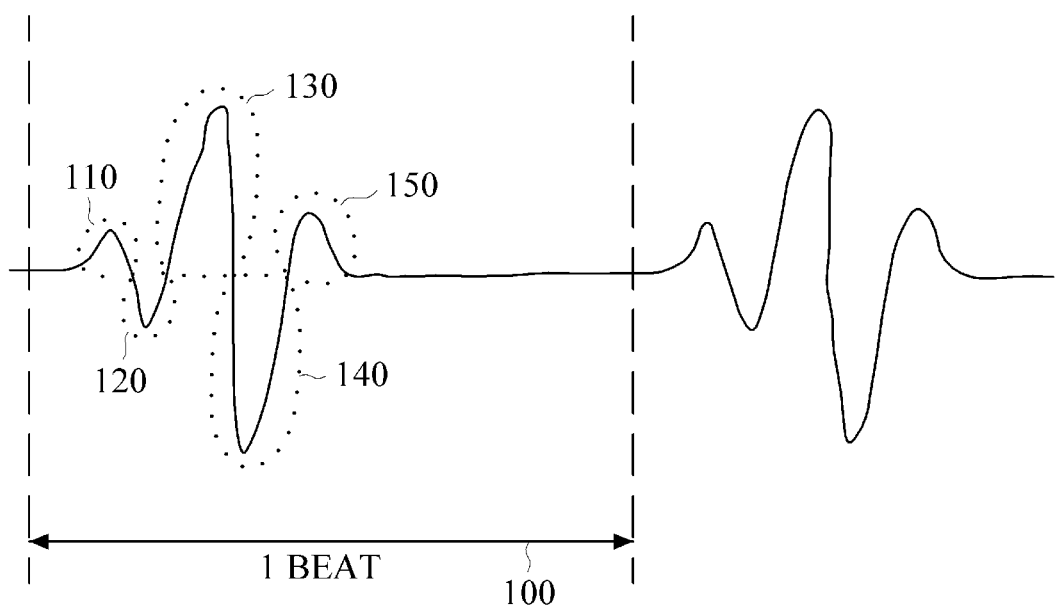
FIG. 1 is a view showing an example of an electrocardiogram.

The following description is provided to assist the reader in gaining a comprehensive understanding of the methods, apparatuses, and/or systems described herein. However, various changes, modifications, and equivalents of the methods, apparatuses, and/or systems described herein will be apparent to those of ordinary skill in the art. Also, descriptions of well-known functions and constructions may be omitted for increased clarity and conciseness.

Throughout the drawings and the detailed description, the same reference numerals refer to the same elements. The relative size and depiction of these elements may be exaggerated for clarity, illustration, and convenience.

FIG. 1 is a view showing an example of an electrocardiogram. An electrocardiogram is an electrical graph representing variations in electrical potential associated with heartbeats with respect to time. A unit representing one heartbeat is called a beat 100. Thus, the electrocardiogram is a graph in which the beat 100 is continuously produced.

When a waveform constituting the beat 100 is analyzed in greater detail, the beat 100 may be divided into a plurality of waves according to a variation in the waveform. In the electrocardiogram, the beat 100 may be divided into a P wave 110, a Q wave 120, an R wave 130, an S wave 140, and a T wave 150. Each wave has one point of inflection, which is called a peak of the wave. As can be seen from FIG. 1, the peaks of the P wave 110, the R wave 130, and the T wave 150 are the highest points of the P wave 110, the R wave 130, and the T wave 150, and the peaks of the Q wave 120 and the S wave 140 are the lowest points of the Q wave 120 and the S wave 140. When the shape of each wave, for instance a position or a magnitude of the peak, is analyzed, it is possible to identify the existence, severity level, etc., of a variety of heart diseases such as angina pectoris, myocardial infarction, and arrhythmia.

Figure 2:
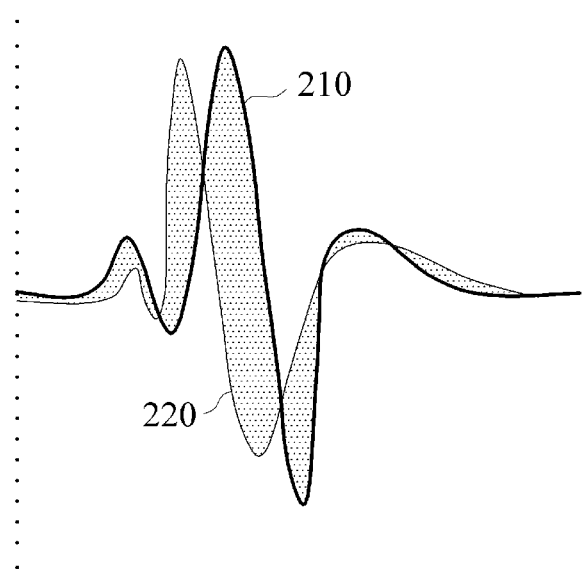
FIG. 2 is a view showing an example in which a reference electrocardiogram and a measured electrocardiogram are displayed in an overlapping state.

FIG. 2 is a view showing an example in which a reference electrocardiogram and a measured electrocardiogram are displayed in an overlapping state. A reference electrocardiogram 210 is extracted from data of a plurality of measured electrocardiograms. The reference electrocardiogram 210 serves as a criterion for determining abnormalities of a measured electrocardiogram 220 and degrees of the abnormalities. An example of the reference electrocardiogram 210 may be an electrocardiogram that statistically extracts a beat having a waveform that is most frequently measured. Another example may be an electrocardiogram that is extracted using a max-min transform analysis. For a statistical analysis, a Gaussian distribution may be used. On the other hand, a normal electrocardiogram may be directly extracted by a skilled doctor.

The reference electrocardiogram 210 may be directly extracted from a plurality of measured electrocardiograms, of the person in question. However, the reference electrocardiogram 210 may be prepared in advance based on a separate standard model or ideal electrocardiogram data. For example, an electrocardiogram that has been previously obtained from a healthy person having the same age and sex as the person being tested may be set as the reference electrocardiogram 210 so that the abnormality in the measured electrocardiogram 220 can be determined. As another example, an electrocardiogram that has been previously obtained from a person having the same heart disease as the person being tested may be set as the reference electrocardiogram 210 so that a severity level of a disease can be determined.

After the reference electrocardiogram 210 is displayed, the measured electrocardiogram 220 is displayed to overlap the reference electrocardiogram 210. That is, the reference electrocardiogram 210 and the measured electrocardiogram 220 are displayed in an overlapping state, so that a deviation between the reference electrocardiogram 210 and the overlapped electrocardiogram 220 can be easily observed with respect to each beat. Alternatively, the deviation may be more clearly visualized by, for instance, displaying shading to show the deviation as shown in FIG. 2.

A pretreatment process of removing a baseline wander from the measured electrocardiogram 220 may be performed in advance. A baseline of the electrocardiogram may be different whenever the measurement is taken due to deep breathing of a person being tested or a positional variation of a sensor. As such, Y-axial baselines of all of the electrocardiograms may be adjusted to coincide with each other using a linear phase filter or discrete wavelet transform, thereby removing the baseline wander. Various techniques for removing baseline wander are well known to one of ordinary skill in the art, and thus will not be described in detail here.

Figure 3:
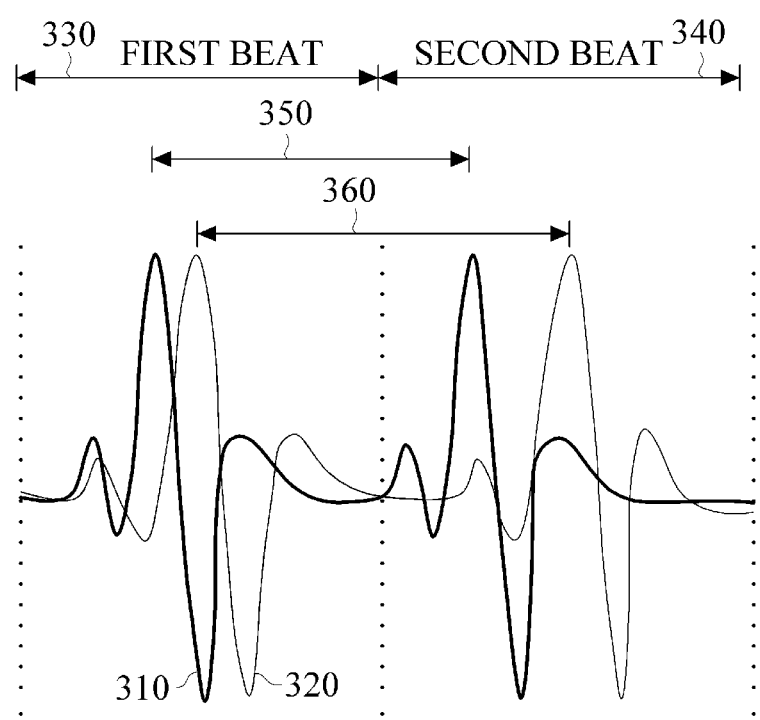
FIG. 3 is a view showing an example in which a reference electrocardiogram and a measured electrocardiogram are displayed in an overlapping state based on a plurality of beats.

FIG. 3 is a view showing an example in which a reference electrocardiogram and a measured electrocardiogram are displayed in an overlapping state based on a plurality of beats. A reference electrocardiogram 310 and a measured electrocardiogram 320 may be displayed in an aligned and overlapping state in units of one beat or in units of a plurality of beats. In FIG. 3, the reference electrocardiogram 310 and the measured electrocardiogram 320 are displayed in an aligned and overlapping state in units of two beats rather than one beat.

In other words, the reference electrocardiogram 310 and the measured electrocardiogram 320 are not aligned at each of first and second beats 330 and 340, but they are aligned taking two beats 330 and 340 as one unit. That is, they are aligned only at the first beat 330. In this way, when the electrocardiograms 310 and 320 are displayed in an aligned and overlapping state based on a plurality of beats, the electrocardiograms 310 and 320 may be displayed so that an interval 350 between R-wave peaks of the reference electrocardiogram 310 the first and second beats 330 and 340 is compared with an interval 360 between R-wave peaks of the measured electrocardiogram 320 in the first and second beats 330 and 340. Thereby, it is possible to check other characteristics of the measured electrocardiogram that are difficult to check when the electrocardiograms are compared based on one beat.

When a reference electrocardiogram and a measured electrocardiogram are displayed in an aligned and overlapping state, a reference point for alignment may be set according to various methods. These methods will be described below in greater detail with reference to FIGS. 4A, 4B, and 5.

Figure 4A:
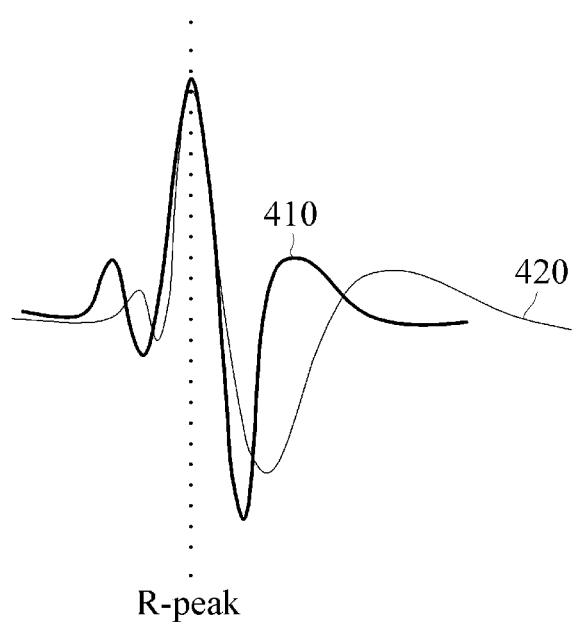
FIGS. 4A and 4B are views showing an example aligning a reference electrocardiogram and a measured electrocardiogram using a single reference point.
Figure 4B:
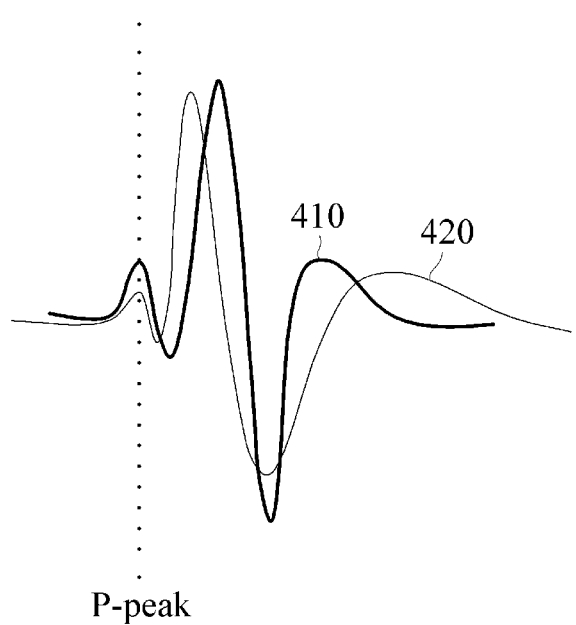

FIGS. 4A and 4B are views showing an example of aligning a reference electrocardiogram and a measured electrocardiogram using a single reference point. In displaying the electrocardiograms in an aligned and overlapping state beat by beat, one reference point may be used in each beat. As one example, in FIG. 4A, the reference electrocardiogram 410 and the measured electrocardiogram 420 are displayed in an overlapping state with R-wave peaks aligned as the reference point. In FIG. 4B, the reference electrocardiogram 410 and the measured electrocardiogram 420 are displayed in an overlapping state with P-wave peaks aligned as the reference point.

Although examples where the R-wave peak and the P-wave peak are used as the reference point have been described with reference to FIGS. 4A and 4B, the electrocardiograms may be aligned using a Q-wave peak, an S-wave peak, a T-wave peak, a start point of a beat, or an end point of a beat as the reference point.

When the reference point for alignment is set for each beat, the measured electrocardiogram 420 is expanded or compressed on a time axis based on this reference point within one beat, thereby causing the reference electrocardiogram 410 and the measured electrocardiogram 420 to be aligned at the reference point of each beat. The measured electrocardiogram 420 may be expanded or compressed on the time axis by using interpolation, for example. Alternatively, instead of the measured electrocardiogram 420 being expanded or compressed on the time axis, the reference electrocardiogram 410 may be expanded or compressed on the time axis, or one of the reference electrocardiogram 410 and the measured electrocardiogram 420 may be expanded on the time axis and the other one of the reference electrocardiogram 410 and the measured electrocardiogram 420 may be compressed on the time axis. The expansion and/or compression compensates for different beat durations in the reference electrocardiogram 410 and the measured electrocardiogram 420 due to different heart rates.

Figure 5:
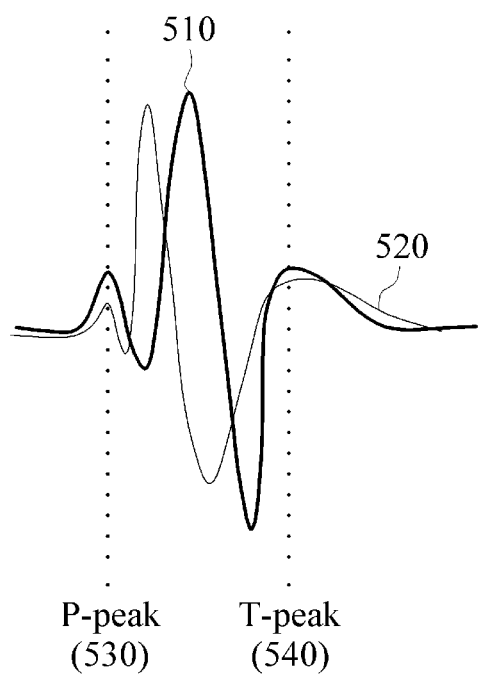
FIG. 5 is a view showing an example of aligning a reference electrocardiogram and a measured electrocardiogram using a plurality of reference points.

FIG. 5 is a view showing an example of aligning a reference electrocardiogram and a measured electrocardiogram using a plurality of reference points. Unlike the examples of FIGS. 4A and 4B in which one reference point in each beat is used for alignment, a plurality of reference points in each beat may be used for alignment as shown in FIG. 5. For example, when a P-wave peak 530 and a T-wave peak 540 in each beat are used as reference points for alignment, a reference electrocardiogram 510 and a measured electrocardiogram 520 may overlap more closely than in the case of alignment using only one reference point in each beat.

When the electrocardiograms are displayed in an overlapping state with the start or end points of the respective beats aligned as the reference point, this is useful to identify arrhythmias capable of being checked based on information about an interval of each waveform, such as atrioventricular conduction block, tachycardia, bradycardia, atrial fibrillation, and the like.

When the electrocardiograms are displayed in an overlapping state with the peaks of the respective waves aligned as the reference point, this is useful to identify arrhythmias capable of being checked based on information about a shape of each wave, such as premature ventricular contraction, premature atrial contraction, and the like.

Figure 6:
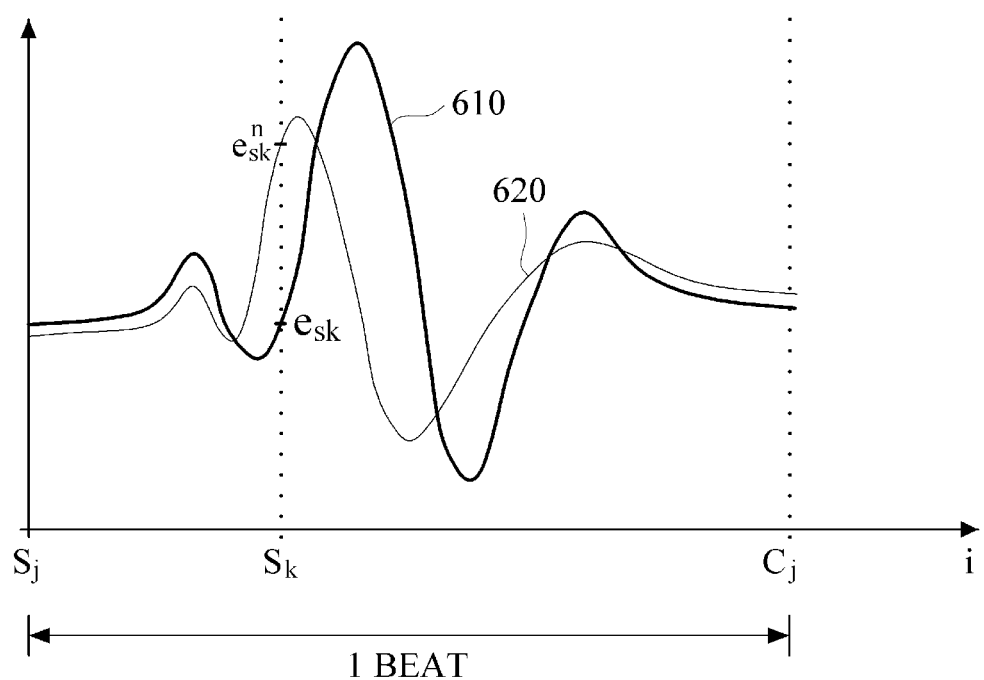
FIG. 6 is a view for explaining an example of calculating a deviation between a reference electrocardiogram and a measured electrocardiogram.

FIG. 6 is a view for explaining an example of calculating a deviation between a reference electrocardiogram and a measured electrocardiogram. After a reference electrocardiogram 610 and a measured electrocardiogram 620 are displayed in an aligned and overlapping state as described above, a deviation between the reference electrocardiogram 610 and the measured electrocardiogram 620 is calculated for one beat. For example, assuming that the start and end points of a j-th beat are $S_j$ and $C_j$, and that a sampling point for calculating the deviation is $S_k$, a value of the reference electrocardiogram 610 at $S_k$ becomes $e_{sk}$, and a value of the measured electrocardiogram 620 at $S_k$ becomes $e''_{sk}$. Then, a deviation $D_j$ between the reference electrocardiogram 610 and the measured electrocardiogram 620 for the j-th beat can be calculated from the following Equation 1:

$$D_j = \sum_{i=S_j}^{C_j} |e_i - e_i^n| \quad (1)$$

When the deviation is calculated, the start and end points of the calculation may be dependent on the aforementioned type of alignment. For example, when the deviation is calculated for one beat, the start and end points of the beat become the start and end points of the calculation. However, when the deviation is calculated based on a plurality of beats as shown in FIG. 3, the start and end points of a set of the beats become the start and end points of the calculation.

The deviation between the electrocardiograms 610 and 620 that has been calculated with for each beat and the deviation between the two electrocardiograms 610 and 620 that has been calculated for a set of a plurality of beats may be displayed on a separate screen apart from the display of the overlapping electrocardiograms 610 and 620. The deviation calculated for each beat may be displayed, or the deviation calculated for a set of a plurality of beats may be displayed. That is, when a large quantity of electrocardiogram data is to be analyzed, and when the deviation is displayed based on a unit of one beat, the displayed deviation becomes bulky. As such, the analyzed data may be compressed over time in a state where the unit is set by a user to include a set of a plurality of beats. A detailed example of displaying the calculated deviation will be described below with reference to FIGS. 7 and 8.

The deviation calculated in this way may be technically referred to as a Minkowski distance, which can be considered to be a generalization of both a Euclidean distance and a Manhattan distance, and may be expressed by the following Equation 2:

$$Lm(A, B) = \sqrt[m]{\sum_{i=1}^{n} (|a_i - b_i|)^m} = \left(\sum_{i=1}^{n} (|a_1 - b_i|)^m\right)^{\frac{1}{m}} \quad (2)$$

Lm is a Minkowski distance; L1 (when m=1) is a Manhattan distance; and L2 (when m=2) is a Euclidean distance. Equation 1 above is an L1 distance calculation, and accordingly the deviation $D_j$ calculated from Equation 1 is a Manhattan distance. Lm distances may be obtained by simple calculations according to the type of distance.

Furthermore, the deviations calculated for each unit may be displayed in a graph, and may be displayed according to a rank. The rank may be a rank among the deviations displayed on one screen, a rank within an entire electrocardiogram range to be analyzed, or a rank within an arbitrary range set by a user.

Figure 7:
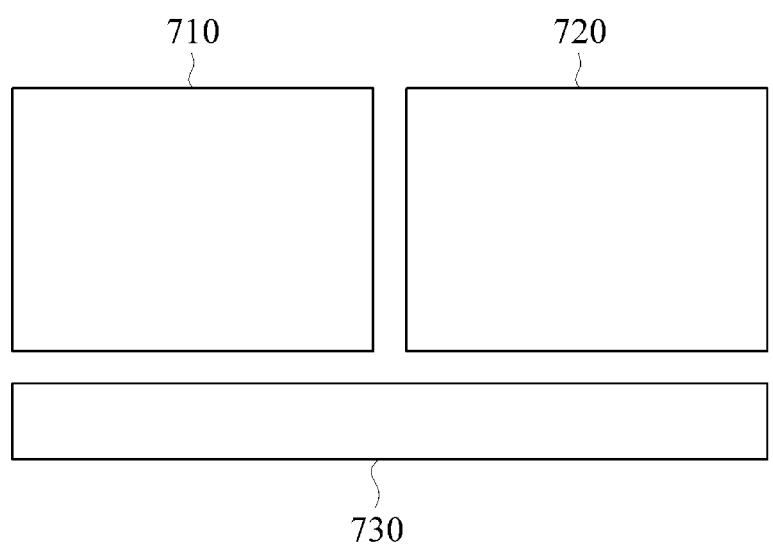
FIG. 7 is a view showing an example of a screen layout for a user interface device for displaying electrocardiograms.

FIG. 7 is a view showing an example of a screen layout for a user interface device for displaying electrocardiograms. The screen layout includes a first display window 710 and a second display window 720, and may further include a setting window 730.

The first display window 710 displays a state where a reference electrocardiogram overlaps a measured electrocardiogram as described above. The second display window 720 displays a deviation between the reference electrocardiogram and the measured electrocardiogram. The deviation may be calculated as described above with reference to FIG. 6. As a method of displaying the calculated value, a bar graph based on each beat, a bar graph based on a plurality of beats, or the like may be used. However, any other type of graph, such as a pie graph, a graph of a broken line, etc., is may be used. Further, the unit of calculation of the deviation may differ according to the selection of a user. As such, the electrocardiogram comparison graph displayed in the first display window 710 may be compressed on the time axis, and be displayed in the second display window 720.

The setting window 730 is a window through which setting details of the graph to be displayed in the first or second display window 710 or 720 are input by a user. The setting window receives a setting of an alignment criterion and a setting of a unit of a calculation of the deviation from the user.

Figure 8:
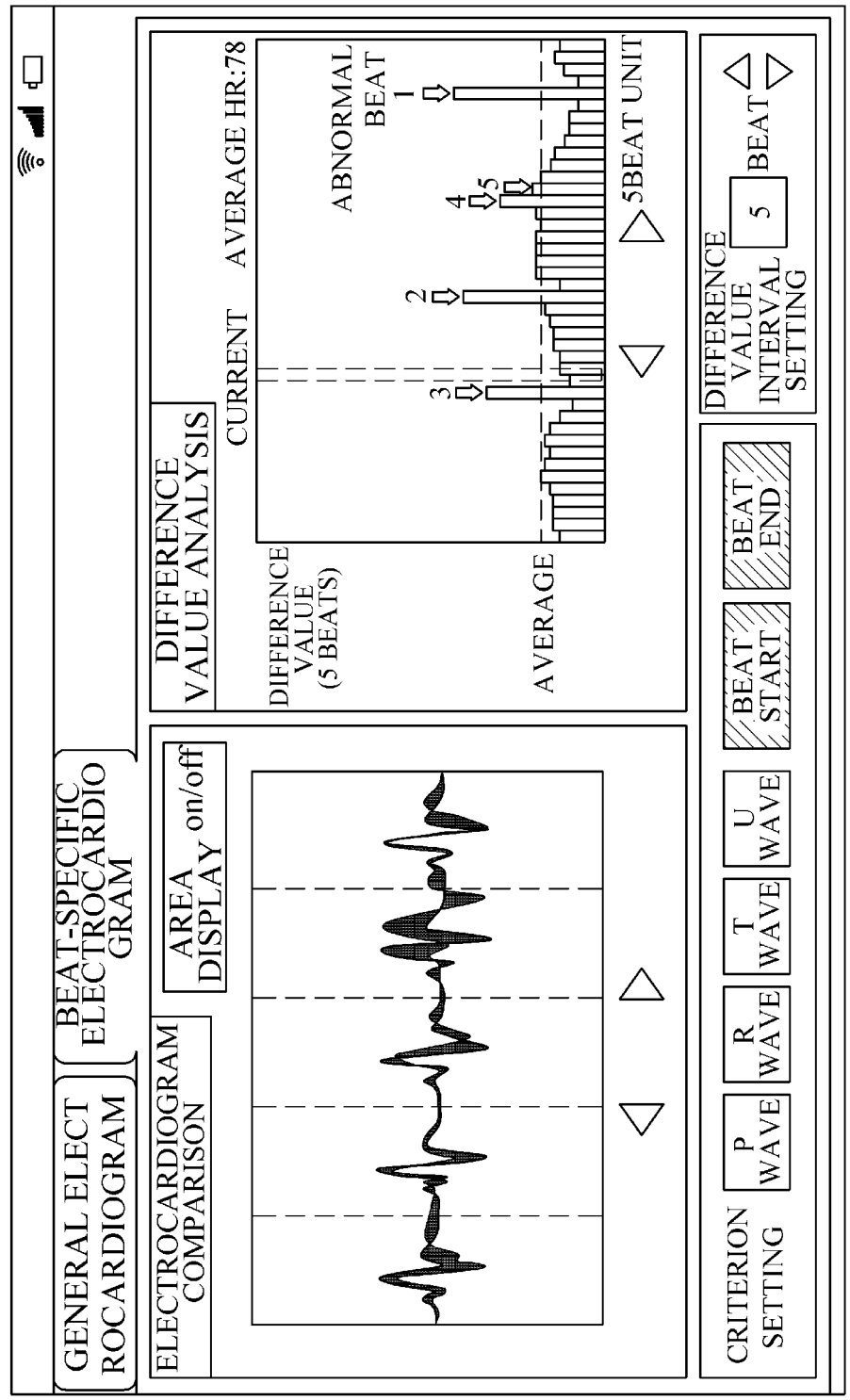
FIG. 8 is a view showing an example of a user interface device displaying electrocardiograms using the screen layout in FIG. 7.

FIG. 8 is a view showing an example of a user interface device displaying electrocardiograms using the screen layout in FIG. 7. For example, overlapping 5-beat electrocardiograms are graphically displayed in a left-hand display window corresponding to the first display window 710 in FIG. 7, and a visualization of a deviation calculated based on a unit of five beats is displayed in a right-hand display window corresponding to the second display window 720 in FIG. 7. Further, the setting of the alignment criterion and setting of the unit of calculation of the deviation may be performed by a user using the bottom window corresponding to the setting window 730 in FIG. 7. In this example in FIG. 8, the alignment is made using start and end points of the beat as reference points as indicated by the shaded buttons labeled "Beat Start" and "Beat End" in the bottom window in FIG. 8.

In addition to the settings, an area display on/off button, a heart rate (HR), and ranks of the deviation values within the currently displayed interval may be additionally displayed. When the area display on/off button is "on," the deviation between the overlapping 5-beat electrocardiograms is displayed with a visual effect or visualization, such as black as shown in FIG. 8, or shading as shown in FIG. 2. However, the deviation may be displayed with any known type of visual effect or visualization. When the area display on/off button is "off," the deviation between the overlapping 5-beat electrocardiograms may be displayed as white, i.e., without any type of visual effect or visualization. In FIG. 8, the numbers 1, 2, 3, 4, and 5 on the arrows in the right-hand display window are ranks. By displaying the ranks in this way, it is possible to more easily discriminate an abnormal beat.

The user interface device described above may be implemented using hardware and/or software components, and may include any type of display that is known in the art.

Figure 9:
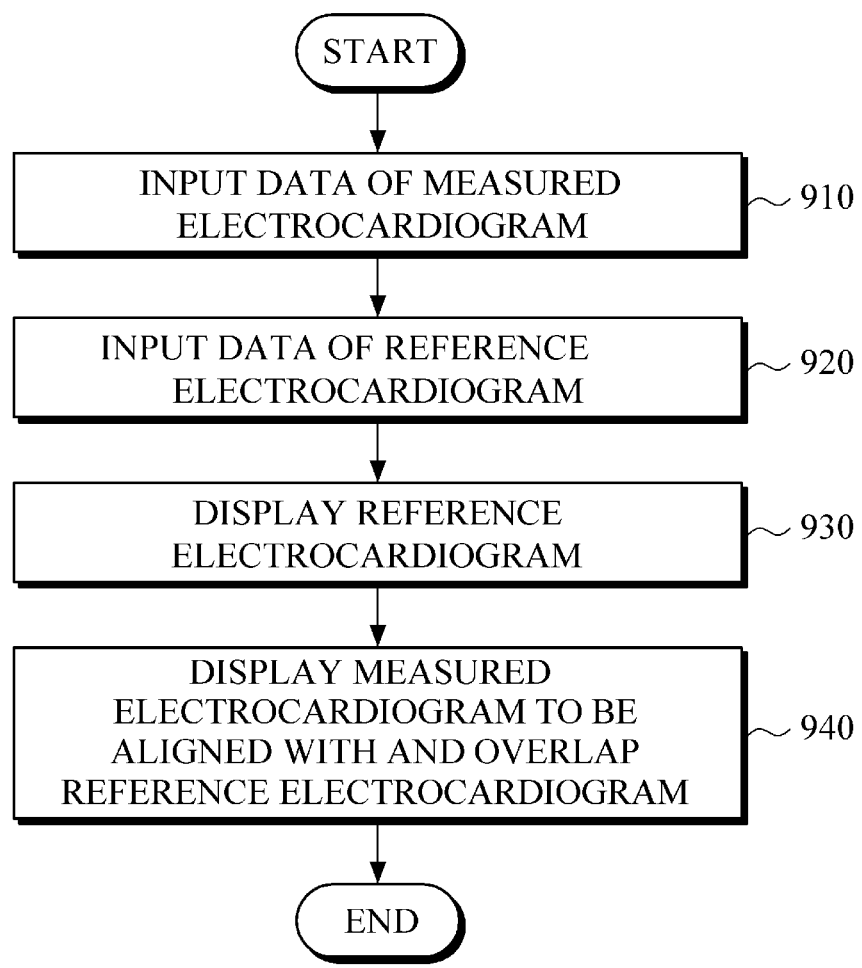
FIG. 9 is a flowchart showing a method of displaying electrocardiograms.

FIG. 9 is a flowchart showing a method of displaying electrocardiograms. First, data of a measured electrocardiogram is input (S910). Next, data of reference electrocardiogram is input (S920). As described above in connection with FIG. 2, the reference electrocardiogram may be extracted from a plurality of measured by a statistical method, or may be prepared in advance based on a standard model or an ideal electrocardiogram data, or may be separately input by a user, as described above.

The reference electrocardiogram is displayed (S930). Next, the measured electrocardiogram is displayed so that it is aligned with and overlaps the reference electrocardiogram (S940). The measured electrocardiogram may be displayed according to various alignment criteria, as described above. For example, the reference electrocardiogram and the measured electrocardiogram may be displayed in an aligned and overlapping state based on one or two or more of a plurality of waves constituting one beat in the electrocardiograms, and/or a start point and/or an end point of a beat or a set for a plurality of beats. These waves may include P, Q, R, S and T waves. The electrocardiograms may be aligned using one or two or more of peaks of the P, Q, R, S and T waves as a reference point. That is, the number of reference points used for alignment may be one or two or more.

The reference electrocardiogram and/or the measured electrocardiogram is expanded or compressed on the time axis based on the reference point or points used for alignment as described above in connection with FIGS. 4A and 4B, thereby causing the electrocardiograms to be aligned with each other at the same reference point at each beat, and then the reference electrocardiogram and the measured electrocardiogram aligned with each other are displayed in an overlapping state. Alternatively, the electrocardiograms may be aligned with each other at the same reference point in a set of a plurality of beats rather than each beat as described above in connection with FIG. 5, and then the reference electrocardiogram and the measured electrocardiogram aligned with each other are displayed in an overlapping state.

Further, a degree of overlapping may be separately visualized and displayed. In greater detail, as described above, the deviation between the reference electrocardiogram and the measured electrocardiogram may be visualized adopting each beat constituting the electrocardiogram as a basic unit, and displayed in a separate window. Alternatively, a deviation calculated based on a plurality of beats as a basic unit rather than one beat may be visualized and displayed. Further, in addition to displaying the deviation, ranks of deviations within a reference range may be displayed.

Figure 10:
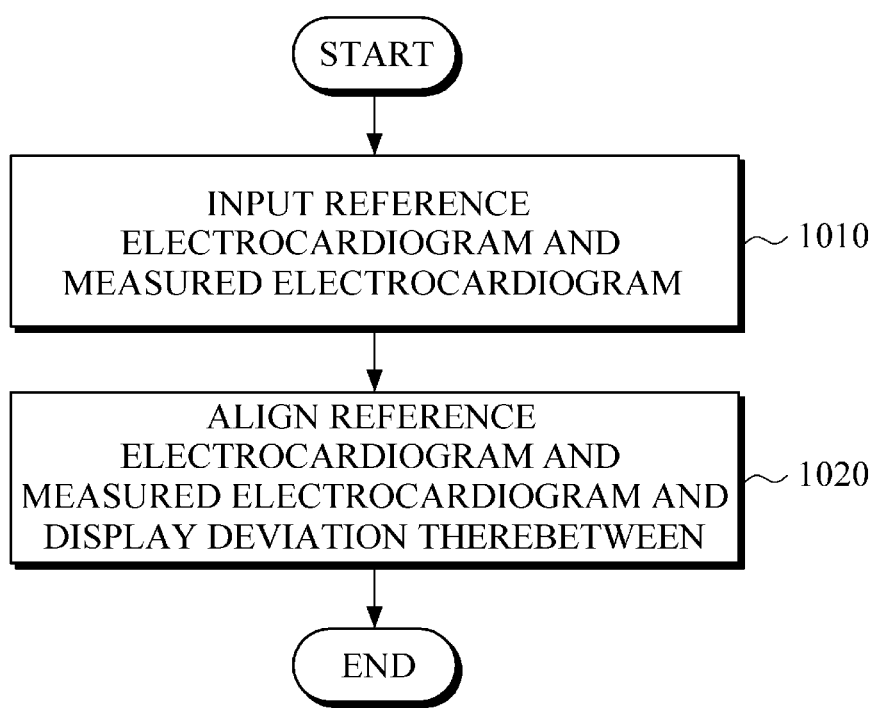
FIG. 10 is a flowchart showing a method of displaying electrocardiograms.

FIG. 10 is a flowchart showing a method of displaying electrocardiograms. A reference electrocardiogram and a measured electrocardiogram are input (S1010). Next, the reference electrocardiogram and the measured electrocardiogram are aligned and a deviation between the reference electrocardiogram and the measured electrocardiogram is visualized and displayed adopting each beat constituting the electrocardiogram as a basic unit as described above (S1020). The electrocardiograms may be aligned based on at least one of a plurality of waves constituting one beat in the electrocardiogram as described above, or in any of the other ways described above. Alternatively, the deviation may be visualized and displayed adopting a set of a plurality of beats as a basic unit as described above. Further, in addition to displaying the deviation, ranks of deviations within a reference range may be displayed.

As described above, in calculating a deviation between a normal electrocardiogram beat and an abnormal electrocardiogram beat, a simple algorithm is used to reduce operation time, so that a diagnosis system can be made small and lightweight.

Further, the electrocardiograms are displayed along with the deviation therebetween on one screen, so that a medical doctor can more easily detect an abnormality of the electrocardiogram with the naked eye. The deviation may be displayed in units of a plurality of beats, so that a large quantity of electrocardiogram data can be more effectively analyzed. The abnormal beats may be ranked and displayed to enable a medical doctor to intuitively observe them, so that a reading time of the electrocardiogram can be greatly reduced.

The various methods described above may be performed using hardware components and/or software components. The user interface device described above may be implemented using hardware and/or software components, and may include any type of display that is known in the art. Software components may be implemented by a processing device, which may be implemented using one or more general-purpose or special-purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purposes of simplicity, the description of a processing device is used as singular; however, one skilled in the art will appreciate that a processing device may include multiple processing elements and multiple types of processing elements. For example, a processing device may include multiple processors or a processor and a controller. In addition, different processing configurations are possible, such a parallel processors.

As used herein, a processing device configured to implement a function A includes a processor programmed to run specific software. In addition, a processing device configured to implement a function A, a function B, and a function C may include configurations, such as, for example, a processor configured to implement functions A, B, and C; a first processor configured to implement function A and a second processor configured to implement functions B and C; a first processor configured to implement functions A and B and a second processor configured to implement function C; a first processor to implement function A, a second processor configured to implement function B, and a third processor configured to implement function C; a first processor configured to implement functions A, B, C and a second processor configured to implement functions A, B, and C, and so on.

The software may include a computer program, a piece of code, an instruction, or some combination thereof, for independently or collectively instructing or configuring the processing device to operate as desired. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion.

In particular, the software and data may be stored by one or more non-transitory computer-readable storage mediums. The non-transitory computer-readable storage medium may include any data storage device that can store data that can be thereafter read by a computer system or processing device. Examples of a non-transitory computer-readable storage medium include read-only memory (ROM), random-access memory (RAM), CD-ROMs, magnetic tapes, floppy disks, and optical data storage devices. Also, functional programs, codes, and code segments for implementing the examples disclosed herein can be easily constructed by programmers skilled in the art to which the examples pertain based on the drawings and their corresponding descriptions as provided herein.

While the invention has been particularly shown and described with reference to examples thereof, it will be understood by those of ordinary skill in the art that various changes in form and details may be made in these examples without departing from the spirit and scope of the invention as defined by the claims and their equivalents. It should be understood that the examples described herein should be considered in a descriptive sense only, and not for purposes of limitation. Descriptions of features or aspects in each example are to be considered as being applicable to similar features or aspects in other examples. Suitable results may be achieved if the described techniques are performed in a different order and/or if components in a described system, architecture, device, or circuit are combined in a different manner and/or replaced or supplemented by other components or their equivalents. Therefore, the scope of the invention is defined not by the detailed description of the disclosure, but by the claims and their equivalents, and all variations within the scope of the claims and their equivalents are to be construed as being included in the invention.

What is claimed is:

1. A method of displaying electrocardiograms on a screen layout of a user interface device, the method comprising, using one or more processors:
    displaying a reference electrocardiogram on a first display window of the screen layout;
    displaying a measured electrocardiogram so that the reference electrocardiogram and the measured electrocardiogram are displayed in an overlapping state on the first display screen; and
    displaying a deviation between the reference electrocardiogram and the measured electrocardiogram in a separate graph from the reference electrocardiogram on a second display screen of the screen layout,
    wherein in response to two beats being displayed successively, aligning the reference electrocardiogram and the measured electrocardiogram at a first beat without aligning the reference electrocardiogram and the measured electrocardiogram at a second beat.

2. The method of claim 1, wherein the reference electrocardiogram and the measured electrocardiogram each comprise one beat;
    each beat of the reference electrocardiogram and the measured electrocardiogram comprise waves; and
    the displaying of the measured electrocardiogram comprises aligning the reference electrocardiogram and the measured electrocardiogram with each other based on one of the waves so that the reference electrocardiogram and the measured electrocardiogram are displayed as being aligned with each in the overlapping state.

3. The method of claim 2, wherein the waves comprise P, Q, R, S, and T waves; and
    the aligning of the reference electrocardiogram and the measured electrocardiogram with each other comprises aligning the reference electrocardiogram and the measured electrocardiogram with each other based on a peak of at least one of the P, Q, R, S, and T waves.

4. The method of claim 3, wherein the aligning of the reference electrocardiogram and the measured electrocardiogram with each other further comprises expanding or compressing the reference electrocardiogram or the measured electrocardiogram on a time axis based on an alignment reference point in each beat so that the reference electrocardiogram and the measured electrocardiogram are displayed as being aligned with each other at a same alignment reference point in each beat in the overlapping state.

5. The method of claim 3, wherein the aligning of the reference electrocardiogram and the measured electrocardiogram with each other further comprises expanding or compressing the reference electrocardiogram or the measured electrocardiogram on a time axis based on an alignment reference point in beats so that the reference electrocardiogram and the measured electrocardiogram are displayed as being aligned with each other at a same alignment reference point in the beats in the overlapping state.

6. The method of claim 1, wherein the reference electrocardiogram is extracted from measured electrocardiograms by a statistical method, or is obtained from a predetermined standard model.

7. The method of claim 1, further comprising
displaying a visualization of the deviation overlapping the display of the reference electrocardiogram and the measured electrocardiogram in the overlapping state.

8. The method of claim 1, wherein the basic unit comprises beats.

9. The method of claim 1, further comprising ranking the deviation within a reference range; and
displaying the ranking of the deviation.

10. The method of claim 1, further comprising displaying the reference electrocardiogram as a solid segment, and displaying the reference ECG as a darker segment compared to the measured ECG.

11. The method of claim 1,
wherein a deviation $D_j$ between the reference electrocardiogram and the measured electrocardiogram for the j-th beat is $$D_j = \sum_{i=S_j}^{C_j} |e_i - e_i^n|$$

wherein $S_j$ and $C_j$ are start and end points of a j-th beat, respectively, $S_k$ is a sampling point for calculating the deviation, $e_{sk}$ is a value of the reference electrocardiogram at $S_k$, and $e''_{sk}$ is a value of the measured electrocardiogram at $S_k$.

12. A method of displaying electrocardiograms on a screen layout of a user interface device, the method comprising, using one or more processors:
receiving a reference electrocardiogram and a measured electrocardiogram each comprising one beat;
aligning the reference electrocardiogram and the measured electrocardiogram with each other on a first display screen of the screen layout; and
displaying a deviation between the reference electrocardiogram and measured electrocardiogram aligned with each other for a basic unit comprising one beat in a separate graph from the reference electrocardiogram on a second display screen of the screen layout,
wherein
in response to two beats being displayed successively, aligning the reference electrocardiogram and the measured electrocardiogram at a first beat without aligning the reference electrocardiogram and the measured electrocardiogram at a second beat so that an interval between R-wave peaks of the reference electrocardiogram is compared with an interval between R-wave peaks of the measured electrocardiogram.

13. The method of claim 12, wherein each beat of the reference electrocardiogram and the measured electrocardiogram comprises waves; and
the aligning of the reference electrocardiogram and the measured electrocardiogram with each other comprises aligning the reference electrocardiogram and the measured electrocardiogram based on one of the waves.

14. The method of claim 12, wherein the basic unit comprises beats.

15. The method of claim 12, further comprising ranking the deviation within a reference range; and
displaying the ranking of the deviation.

16. A method of displaying electrocardiograms on a screen layout of a user interface device, the method comprising, using one or more processors:
obtaining a reference electrocardiogram;
obtaining a measured electrocardiogram;
aligning the reference electrocardiogram and the measured electrocardiogram with each other at one alignment reference point;
displaying the reference electrocardiogram and the measured electrocardiogram aligned with each other at the one alignment reference point in an overlapping state on a first display screen of the screen layout;
displaying a deviation between the reference electrocardiogram and the measured electrocardiogram in a separate graph from the reference electrocardiogram on a second display screen of the layout,
wherein in response to two beats being displayed successively, aligning the reference electrocardiogram and the measured electrocardiogram at a first beat without aligning the reference electrocardiogram and the measured electrocardiogram at a second beat.

17. The method of claim 16, wherein the reference electrocardiogram and the measured electrocardiogram each comprise one beat; and
the aligning comprises aligning the reference electrocardiogram and the measured electrocardiogram with each other at one alignment reference point within each beat.

18. The method of claim 16, wherein the reference electrocardiogram and the measured electrocardiogram each comprise beats;
the aligning comprises aligning the reference electrocardiogram and the measured electrocardiogram with each other at one alignment reference point within a set of the beats; and
the displaying comprises displaying the reference electrocardiogram and the measured electrocardiogram aligned with each other at the one alignment reference point in an overlapping state for the set of the beats.

19. The method of claim 16, wherein the reference electrocardiogram and the measured electrocardiogram each comprise one beat; and
the method further comprises expanding and/or compressing the reference electrocardiogram and/or the measured electrocardiogram on a time axis so that a length of each beat of the reference electrocardiogram is equal to a length of each beat of the measured electrocardiogram when the reference electrocardiogram and the measured electrocardiogram aligned with each other at the one alignment reference point are displayed in the overlapping state.

20. The method of claim 16, wherein the reference electrocardiogram and the measured electrocardiogram each comprise beats; and
the method further comprises expanding and/or compressing the reference electrocardiogram and/or the measured electrocardiogram on a time axis so that a length of a set of beats of the reference electrocardiogram is equal to a length of a set of beats of the measured electrocardiogram in response to the reference electrocardiogram and the measured electrocardiogram aligned with each other at the one alignment reference point being displayed in the overlapping state.

21. The method of claim 16, wherein the reference electrocardiogram and the measured electrocardiogram each comprise one beat;
each beat of the reference electrocardiogram and the measured electrocardiogram comprises waves; and the one alignment reference point comprises any one or any combination of the following:
　a start point of a beat;
　an end point of a beat; and
　a peak of one of the waves.

22. The method of claim 16, wherein the reference electrocardiogram and the measured electrocardiogram each comprise beats;
　each beat of the reference electrocardiogram and the measured electrocardiogram comprises waves; and
　the one alignment reference point comprises any one or any combination of the following:
　　a start point of a set of beats;
　　an end point of a set of beats; and
　　a peak of one of the waves.

23. The method of claim 16, further comprising displaying a visualization of the deviation overlapping with the display of the reference electrocardiogram and the measured electrocardiogram aligned with each other at the one alignment reference point in the overlapping state.

24. The method of claim 16, further comprising:
　calculating the deviation between the reference electrocardiogram and the measured electrocardiogram aligned with each other;
　generating a visualization of the deviation; and
　displaying the visualization of the deviation.

25. The method of claim 24, wherein the reference electrocardiogram and the measured electrocardiogram each comprise one beat; and
　the calculating comprises calculating the deviation for one beat of each of the reference electrocardiogram and the measured electrocardiogram.

26. The method of claim 24, wherein the reference electrocardiogram and the measured electrocardiogram each comprise beats; and
　the calculating comprises calculating the deviation for a set of beats of each of the reference electrocardiogram and the measured electrocardiogram.

27. The method of claim 24, further comprising ranking the deviation within a reference range; and
　displaying the ranking of the deviation.

\* \* \* \* \*